United States Patent
Hammonds et al.

(10) Patent No.: US 10,520,374 B1
(45) Date of Patent: Dec. 31, 2019

(54) PHONON EFFECT BASED NANOSCALE TEMPERATURE MEASUREMENT

(71) Applicants: James S. Hammonds, New York, NY (US); Kimani A. Stancil, Baltimore, MD (US)

(72) Inventors: James S. Hammonds, New York, NY (US); Kimani A. Stancil, Baltimore, MD (US)

(73) Assignee: HOWARD UNIVERSITY, Washington, DC (US)

( * ) Notice: Subject to any disclaimer, the term of this patent is extended or adjusted under 35 U.S.C. 154(b) by 159 days.

(21) Appl. No.: 15/258,926

(22) Filed: Sep. 7, 2016

Related U.S. Application Data

(60) Provisional application No. 62/217,182, filed on Sep. 11, 2015.

(51) Int. Cl.
*G01K 19/00* (2006.01)
*G01J 5/00* (2006.01)
*G01N 24/00* (2006.01)
*H01S 3/00* (2006.01)

(52) U.S. Cl.
CPC ............... *G01K 19/00* (2013.01); *G01J 5/00* (2013.01); *G01K 2211/00* (2013.01); *G01N 24/004* (2013.01); *H01S 3/0014* (2013.01)

(58) Field of Classification Search
None
See application file for complete search history.

(56) References Cited

U.S. PATENT DOCUMENTS

| | | | | |
|---|---|---|---|---|
| 2006/0067605 A1* | 3/2006 | Mirkarimi | ............ | B82Y 20/00 385/12 |
| 2011/0261851 A1* | 10/2011 | Malpuech | ............ | B82Y 20/00 372/45.01 |
| 2013/0044314 A1* | 2/2013 | Koulikov | ........... | G01N 21/1702 356/72 |
| 2014/0326902 A1* | 11/2014 | Tahan | ................... | H01L 49/006 250/493.1 |

OTHER PUBLICATIONS

Yin et al., "Fiber Ring Laser Sensor for Temperature Measurement" Journal of Lightwave Technology, vol. 28, No. 23, Dec. 1, 2010 (Year: 2010).*

(Continued)

*Primary Examiner* — John C Kuan
(74) *Attorney, Agent, or Firm* — Sughrue Mion, PLLC

(57) ABSTRACT

In some embodiments, phonon based temperature measuring apparatuses include a light source positioned to direct a light toward a prism-resonant cavity interface of an optical resonant cavity inducing an evanescent wave that is guided into the resonant cavity having surface phonon polariton properties; a detector positioned proximate the resonant cavity and configured to detect reflected light from the prism-resonant cavity interface; and a temperature calculator coupled with the detector and configured to determine evanescent light coupling to one or more phonon polariton modes from the resonant cavity, calculate a quality factor as a function of a frequency spectrum of at least one of the one or more phonon polariton modes, and determine a temperature of a dielectric material within the resonant cavity as a function of the quality factor.

22 Claims, 8 Drawing Sheets

(56) References Cited

OTHER PUBLICATIONS

Wang et al., "Optical Properties of Single Infrared Resonant Circular Microcavities for Surface Phonon Polaritons" American Chemical Society, Nano Letters 2013, 13, 5051-5055 (Year: 2013).*
Socorro et al., "Temperature sensor based on a hybrid ITO-silica resonant cavity" Optics Express, vol. 23, No. 3, 2015 (Year: 2015).*
Andersen, T. B. et al.; "Compact on-Chip Temperature Sensors Based on Dielectric-Loaded Plasmonic Waveguide-Ring Resonators"; Sensors vol. 11 Issue 2; Feb. 7, 2011; pp. 1992-2000.
Andrade, A. A. et al.; "Thermal lens determination of the temperature coefficient of optical path length in optical materials"; Review of Scientific Instruments vol. 74 Issue 1; Jan. 16, 2003; pp. 877-880.
Ash, E. A. et al.; "Super-resolution Aperture Scanning Microscope"; Nature vol. 237; Jun. 30, 1972; pp. 510-512.
Babuty, A.; "Blackbody Spectrum Revisited in the Near Field"; Physical Review Letters vol. 110; Apr. 5, 2013; pp. 146103-1-146103-5.
Begtrup, G.E. et al.; "Probing Nanoscale Solids at Thermal Extremes"; Physical Review Letters vol. 99; Oct. 12, 2007; pp. 155901-1155901-4.
Bejan, A.; Advanced Engineering Thermodynamics Third Edition; Wiley; 2006; pp. 126-129.
Brintlinger, T. et al.; "Electron Thermal Microscopy"; Nano Letters vol. 8; Jan. 30, 2008; pp. 582-585.
Brites, C. et al.; "Thermometry at the nanoscale"; Nanoscale vol. 4; May 1, 2012; pp. 4799-4829.
Cahill, D. G. et al.; "Nanoscale thermal transport"; Journal of Applied Physics vol. 93 Issue 2; Jan. 15, 2003; pp. 793-818.
Chen, D.-Z. et al.; "Measurement of silicon dioxide surface phonon-polariton propagation length by attenuated total reflection"; Applied PHysics Letters vol. 91; Sep. 19, 2007; pp. 121906-1-121906-3.
Dahan, N. et al.; "Space-variant polarization manipulation of a thermal emission by a SiO2 subwavelength grating supporting surface phonon-polaritons"; Applied Physics Letters vol. 86 Issue 19; May 2, 2005; pp. 191102-1-191102-3.
Davis III, L. J. et al.; "Surface plasmon based thermo-optic and temperature sensor for microfluidic thermometry"; Review of Scientific Instruments vol. 81 Issue 11, 114905; 2010; pp. 1-18.
Galliou, S. et al.; "Outstanding Quality Factors of Bulk Acoustic Wave Resonators at Cyogenic Temperature"; Proceedings of European Frequency and Time Forum, Toulouse, France; 2008; 5 pages.
Greffet, J. J. et al.; "Coherent emission of light by thermal sources"; Nature vol. 416; Mar. 7, 2002; pp. 61-64.

Hammonds, J. S. et al.; "Quality factor temperature dependence of a surface phonon polariton resonance cavity"; Applied Physics Letters vol. 105; Sep. 18, 2014; pp. 114107-1-114107-4.
Nutter, E. et al.; "Exploitation of Localized Surface Plamon Resonance"; Advanced Materials vol. 16 Issue 19; Oct. 4, 2004; pp. 1685-1706.
Kim, B. et al.; "Temperature Dependence of Quality Factor in MEMS Resonators"; Journal of Microelectromechanical Systems vol. 17 Issue 3, 755; Jun. 6, 2008; 4 pages.
Le Gall, J. et al.; "Experimental and theoretical study of reflection and coherent thermal emission by a SiC grating supporting a surface-phonon polariton"; Physical Review B vol. 55 Issue 15; Apr. 15, 1997; pp. 10105-10114.
Lee, L. et al.; "Gazing Into the Void: What You Can Do With Vantablack, the Darkest Material Ever Made"; https://www.nytimes.com/2014/11/06/garden/what-you-can-do-with-vantablack-the-darkest-material-ever-made.html?emc=eta1&_r=0; The New York Times; Nov. 5, 2014; pp. 1-3.
Liu, W.-T. et al.; "Sum-frequency phonon spectroscopy on α-quartz"; Physical Review B vol. 78; Jul. 23, 2008; pp. 024302-1-024302-6.
Liu, W.-T. et al.; "Surface Vibrational Modes of α-Quartz(0001) Probed by Sum-Frequency Spectroscopy"; Physcial Review Letters vol. 101; Jul. 1, 2008; pp. 016101-1-016101-4.
O'Haver, T. C.; "Interactive Signal Processing Tools"; https://terpconnect.umd.edu/~toh/spectrum/SignalProcessingTools.html; Accessed on Sep. 15, 2014; pp. 1-14.
Raether, H.; "Surface Plasmons on Smooth Surfaces"; Surface Plasmons on Smooth and Rough Surfaces and on Gratings Chapter 2; Springer-Verlag; 1988; pp. 4-39.
Shen, S. et al.; "Surface Phonon Polaritons Mediated Energy Transfer between Nanoscale Gaps"; Nano Letters vol. 9 Issue 8; Jul. 2, 2009; pp. 2902-2913.
Srivastava, T. et al.; "Highly Sensitive Plasmonic Temperature Sensor Based on Photonic Crystal Surface Plasmon Waveguide"; Plasmonics vol. 8 Issue 2; Aug. 16, 2012; pp. 515-521.
Wikipedia; "Evanescent wave"; http://en.wikipedia.org/wiki/Evanescent_wave; Accessed on Nov. 12, 2014; pp. 1-6.
Willets, K. A. et al.; "Localized Surface Plasmon Resonance Spectroscopy and Sensing"; Annual Reviews Physical Chemistry vol. 58; May 5, 2007; pp. 267-297.
Wu, X. et al.; "The material dependence of temperature measurement resolution in thermal scanning electron microscopy"; Applied Physics Letter vol. 102 Issue 11; 2013; pp. 113107-1-1131007-5.
Vinogradov, E.A. et al.; "Chapter 4 Thermally Stimulated Emission of Surface Polaritons"; Surface Polaritons; North-Holland; 1982; pp. 145-184.

* cited by examiner

| Reference peak (cm$^{-1}$) | 795 | 1064 | 1111 | 1160 | 795 | 960 | 960 | 1111 |
|---|---|---|---|---|---|---|---|---|
| Peak fit (cm-1) | 766.1586 | 1069.671 | 1119.729 | 1169.271 | 801.9957 | 916.1329 | 1005.884 | 1097.143 |
| STD | 31.96713 | 10.25292 | 14.92534 | 15.01141 | 3.429372 | 18.49387 | 10.62418 | 6.284865 |

TABLE 1: Detailed Gaussian curve fit

FIG. 9

PHONON EFFECT BASED NANOSCALE TEMPERATURE MEASUREMENT

CROSS-REFERENCE TO RELATED APPLICATION

This application claim the benefit of U.S. Provisional Application No. 62/217,182, filed Sep. 11, 2015, for Hammnds et al., and entitled PHONON EFFECT BASED NANOSCALE TEMPERATURE MEASUREMENT, which is incorporated herein by reference in its entirety.

TECHNICAL FIELD

The present disclosure relates generally to measuring temperature. More specifically, the present disclosure relates to measuring temperature in nanoscale systems.

BACKGROUND

Many systems measure temperature. The ability to sense temperature changes in small scale systems is becoming increasingly important. Some systems allow for small scale temperature measurements. These systems, however, are often impractical for many applications because they require specialized conditions and/or impractical equipment. Similarly, many systems are impractical and/or do not operate with many technology areas.

For example, the ability to sense temperature changes in nanoscale systems is becoming increasingly important in application areas such as but not limited to microelectronics, microfluidics, nanomedicine, and other such fields. Such application areas and/or fields can benefit from accurate temperature measurements with submicron (e.g., hundreds of nanometers and in some instances tens of nanometers) resolution.

Optical based temperature measurement approaches such as thermoreflectance are diffraction limited and thus the spatial resolution is limited by the wavelength of light used in the analysis. Non-diffraction limited approaches can involve electron microscopy. For example, some systems use transmission electron microscopy (TEM) to achieve temperature mapping with submicron resolution. However, these systems are generally impractical for many applications since they require specialized conditions such as an evacuated chamber. Submicron temperature measurements may also be possible with near-field scanning optical microscopy (NSOM), which uses a nanoscale fiber or metallic tip. The use of NSOM analysis is relatively restricted since vacuum or cryogenic temperatures are typically necessary.

SUMMARY

A phonon based temperature measuring apparatus and method allows for precise temperature measurements in a difficult setting, such as in a submicron sized chamber in which controlled chemical or biological processes take place. For example, some embodiments provide temperature measurements with submicron (e.g., less than thousands of nanometers and in some instances hundreds of nanometers) resolution. Some embodiments utilize the surface phonon polaritons (SPhP), an infra-red (IR) resonance mode to measure the temperature. A common interpretation of a polariton is a description of coupling between an elementary excitation (like a phonon or plasmon), and a photon. However both surface plasmonic behavior, and phononic behavior can be considered when making new devices composed of combinations of metal, semiconductor, or dielectric (insulator). Surface plasmons are observed in metals. This mode is excited by incident visible light. By using a polar crystalline material such as $SiO_2$ or SiC analogous localized surface phonon modes can be excited characterized by a displaced crystalline lattice versus a displaced electron cloud that is excited in metals. For surface phonon-polaritons, the electromagnetic evanescent wave and lattice vibration waves are coupled. Surface phonon (SPh) modes are excited by infrared light, which can make the phonon modes appropriate for IR light applications. The manipulation of the physics of SPhP modes by tuning the associated nanoscale geometries can contribute to the development of next-generation small, portable, extremely sensitive infrared sensing devices and novel energy conversion systems. This provides for an expanded or exotic system of temperature sensors where the geometric dispersion of surface phonons results from nanoparticle arrays of polar materials. The surface phonon would arise as a point sensor based on its localization upon each nanoparticle. The spacing between nanoparticles and between nanoparticle arrays can be adjusted to effect the transport of thermal radiation across the nanoparticles or across their clusters. This disclosure describes approaches where a phonon polariton is used to determine temperature in the phonon polariton's environment.

The development of surface phonon polariton based thermometry has broader applicability than other temperature sensing systems that provide submicron resolution at least in part because of the accuracy of measurements obtained, the ability to take advantage of a variety of coupling modes, and more compact optical sources. The ability to sense temperature changes in nanoscale systems is becoming increasingly important in application areas such as but not limited to microelectronics, microfluidics, nanomedicine, and other such technical areas, which can be improved through temperature measurement with submicron (100s of nanometers) resolution such as is possible with surface phonon polariton based thermometry. As described herein, surface phonon polariton based thermometry can take advantage of a variety of coupling modes. For instance, certain approaches take advantage of near-field effects in sensing temperature changes. With the use of a Fourier Transform Infra-Red spectrometer with Attenuated Total Internal Reflection (FTIR-ATR), phonon-polariton coupling may be realized by an infra-red beam incident upon a material interface with a suitable mismatch in refraction index so that an evanescent wave may be created. A silicon dioxide film and/or substrate, a silicon carbide film and/or substrate, or other such material is surface sensitive to the evanescent field over short or nanoscale distances for directions that are perpendicular to the material interface. The evanescent field interaction with the surface results in resonant coupling. The ability to monitor and couple to plasmonic- or phononic-polariton resonance modes is estimated by a material and geometry specific propagation distance. Plasmonic modes at metal/dielectric interfaces can typically propagate tens to hundreds of microns, while optical phonon polariton propagation at silicon carbide thin film/dielectric interfaces can in at least some instances be thousands of microns. The longer propagation distances associated with phonon resonances implies an easier coupling, or that phononic optical systems may more readily, or simply be easily designed. Further, phononic optical systems may be configured with more compact optical sources. To measure the temperature, geometry and confinement is used in some implementations to effect a resonant cavity for determining how long lived the surface resonance modes are through a quality factor, Q. The quality factor's dependence on the resonant cavity size, provides an empirical measure of the temperature, directly linking the sensing of nanoscale thermal radiation by surface phonon-polariton coupling to nanoscale temperature sensing. In addition, for example, some embodiments take advantage of nanoscale thermal radiation and/or optical phonon resonance at the surface of a material (e.g., silicon carbide, silica, etc.) that can be pumped by thermal energy alone (e.g., heating), which allows for some embodiments to provide spectrally selective thermal emitters that are designed for exploiting optical phonon resonance.

Further, certain approaches utilize the dependence of phononic resonances on temperature and sense temperature using phononic resonances to provide phononic thermosensors. For example, some embodiments determine and/or estimate the temperature dependence of optical phonon resonance modes confined to a metal-$SiO_2$-diamond-dielectric resonance cavity through a determination and/or estimation of a cavity quality factor and/or variations in the cavity quality factor relative to variations in an optical path and/or width. The optical width can then be related to the dielectric thermo-optical properties to obtain an estimate of the quality factor dependence on temperature.

Still further, some embodiments utilize the surface phonon polariton coupling in an optical resonant cavity. For example, some implementations utilize a silicon dioxide optical resonant cavity with metal or metal coated walls (e.g., 250 nm gold and chromium side walls). A temperature dependence of the quality factor, $Q=\omega_0/\Delta\omega$, is utilized in determining a temperature of a dielectric material within the cavity. For example, some embodiments utilize an FTIR-ATR to detect light, perform relevant measurements and/or perform calculations in determining relevant parameters to identify a temperature and/or a change in temperature from an equilibrium temperature. Further, in some instances, the FTIR-ATR spectrometer generates an evanescent wave by directing light to a prism. This evanescent wave, in-turn, is coupled to lattice vibrations inside a resonant cavity situated on the prism. The coupled evanescent wave and lattice vibration is called a surface phonon polariton (SPhP), which transports energy along and/or away from the material interface. Thus the incident FTIR-ATR spectrometer light is "transformed" into an SPhP within the cavity, causing the reflected light intensity from the cavity to be less than the incident light intensity at a particular wave number or frequency (that depends on the material or dielectric). The reduction in light intensity is detected by the spectrometer. For the resonant cavity geometry, the reduced intensity of the light spectra at, and near, the SPhP frequency depends on the ratio of the SPhP wave energy reflection rate at the metal cavity walls, to the SPhP wave energy lost from the cavity (via transmission and absorption), and this ratio depends on the cavity width (or size). The ratio of SPhP reflections to losses in the cavity is equivalent to the quality factor, which is directly proportional to the mode lifetime. The temperature can be determined, in some implementations, using the general thermo-optical coefficient and the temperature dependence of the quality factor. In many embodiments, the temperature dependence of the quality factor is a practical and almost universal result that describes the energy dissipative behavior of mechanically responsive systems, optically responsive systems, and/or other such systems.

In some embodiments, a phonon based temperature measuring apparatus includes a light source positioned to direct a light toward a prism-resonant cavity interface of an optical resonant cavity. The light source induces an evanescent wave that is guided into the resonant cavity having surface phonon polariton properties. A detector positioned proximate the resonant cavity detects reflected light from the prism-resonant cavity interface. A temperature calculator is operatively coupled to the detector and configured to determine evanescent light coupling to one or more phonon polariton modes from the resonant cavity, calculate a quality factor as a function of a frequency spectrum of at least one of the one or more phonon polariton modes, and determine a temperature of a dielectric material within the resonant cavity as a function of the quality factor.

A corresponding method of measuring nanoscale temperature includes directing light toward a prism-resonant cavity interface having surface phonon polariton properties and detecting reflected light. The method further includes determining, from the detected reflected light, light coupling to one or more phonon polariton modes from the resonant cavity and calculating a quality factor as a function of a frequency spectrum of at least one of the one or more phonon polariton modes. A temperature of a dielectric material within the resonant cavity is determined as a function of the quality factor.

Further, some embodiments provide a phonon based temperature measuring apparatus including a resonant cavity with a substrate having surface phonon polariton properties and opposing reflective walls extending from a substrate surface of the substrate defining boundaries of the resonant cavity. Each of the reflective walls has a metallic reflective face with the reflective faces being separated by a width of the resonant cavity and configured to aid in retaining a dielectric within the resonant cavity. The resonant cavity is configured to exhibit, in response to polarized light directed into the resonant cavity, surface phonon polariton excitation of the substrate that is dependent on a temperature of the dielectric.

BRIEF DESCRIPTION OF THE DRAWINGS

FIG. 9 shows a Table listing determined peaks and their standard deviations, in accordance with some embodiments.

Figure 1:
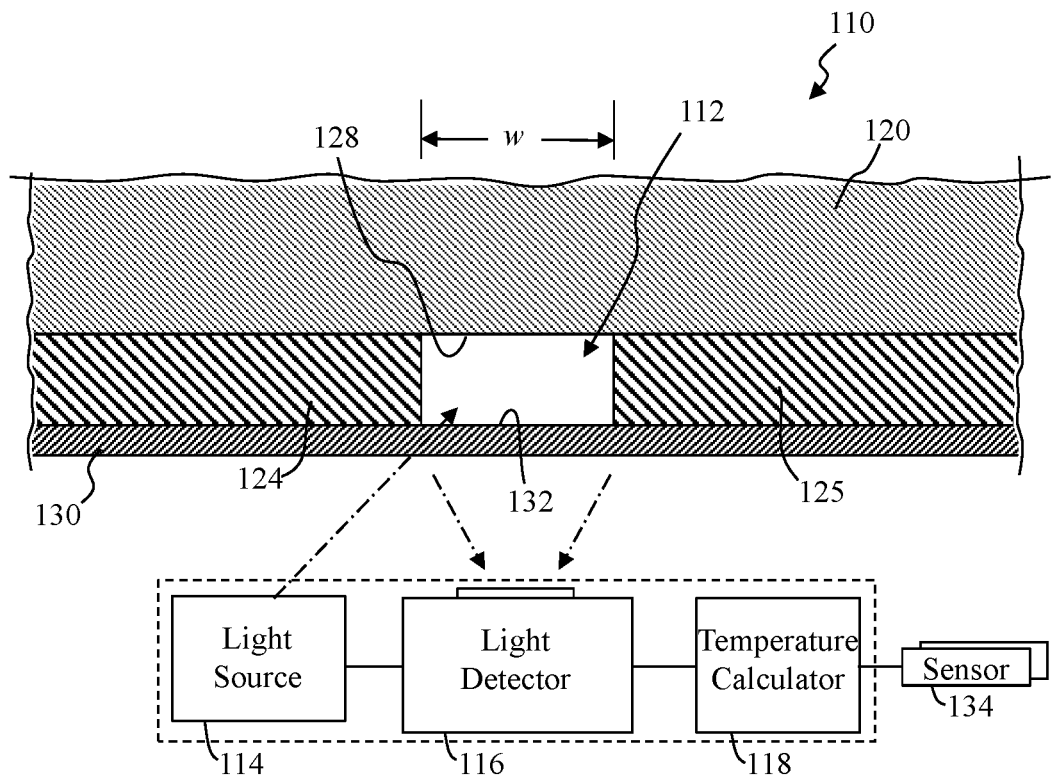
FIG. 1 shows a simplified block diagram of an exemplary temperature measurement system with an enlarged cross-sectional view of an exemplary optical resonant cavity, in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Reference throughout this specification to "one embodiment," "an embodiment," "some embodiments," "some implementations" or similar language means that a particular feature, structure, or characteristic described in connection with the embodiment is included in at least one embodiment of the present invention. Thus, appearances of the phrases "in one embodiment," "in an embodiment," "in some embodiments," and similar language throughout this specification may, but do not necessarily, all refer to the same embodiment.

Furthermore, the described features, structures, or characteristics of the invention may be combined in any suitable manner in one or more embodiments. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

As introduced above, optical based temperature measurement approaches such as thermoreflectance are diffraction limited and thus the spatial resolution is limited by the wavelength of light used in the analysis. Non-diffraction limited approaches can involve electron microscopy. For example, some systems use transmission electron microscopy (TEM) to achieve temperature mapping with submicron resolution. However, these systems are generally impractical for many applications since they require specialized conditions such as an evacuated chamber. Submicron temperature measurements may also be possible with near-field scanning optical microscopy (NSOM), which uses a nanoscale fiber or metallic tip. The use of NSOM analysis is relatively restricted since vacuum or cryogenic temperatures are typically necessary. Scanning thermal microscopy (SThM) also employs a temperature-sensing tip to probe the surface of a sample. The SThM approach requires detailed understandings of the heat transfer mechanisms between the sample and the tip for accurate temperature estimation, and has only been demonstrated for solid samples. Non-contact methods include different approaches to fluorescence thermography, which can achieve submicron resolution, but these techniques require highly sensitive sources and detectors, causing them to be very expensive. Other non-diffraction limited approaches have been demonstrated that use evanescent light, however the light used visible wavelengths.

With reference to the drawings, FIG. 1 shows a simplified block diagram of an exemplary temperature measurement apparatus 110 with an enlarged cross-sectional view of an exemplary optical resonant cavity 112. The apparatus includes the resonant cavity 112, a light source 114, a light detection system or light detector 116, and a calculation system or temperature calculator 118, which may each comprise separate hardware elements or be combined into a single hardware element with one or more processing devices configured to control the hardware in the manners described herein. The resonant cavity 112 is configured to have surface phonon polariton properties. In some embodiments, the resonant cavity 112 is formed on and/or within a substrate 120. Optionally, the resonant cavity 112 is a microscale or nanoscale resonant cavity. The resonant cavity 112 is formed between opposing reflective walls 124-125 extending from a substrate surface 128 of the substrate. The reflective walls define side boundaries of the resonant cavity.

In some embodiments, the resonant cavity is enclosed by a cover 130, lid, or other such closure structure, and/or a cover is positioned adjacent the cavity. Further, in some implementations, the cover includes and/or is a prism, crystal, lens, or other similar structure. For simplicity, the cover is referred to below as a prism 130; however, it will be appreciated by those skilled in the art that in some implementations, the cover may be and/or main include one or more prisms, lenses, crystals, sheets, plates or other such structure. Typically, the prism is at least partially transparent to one or more ranges of wavelengths of light directed at the resonant cavity (e.g., infrared, near infrared, or other such ranges of wavelengths or combinations of such ranges). In the illustrated example, the prism 130 is positioned relative to at least the cavity and establishes a prism-resonant cavity interface 132.

Typically, the walls 124-125 comprise reflective faces with the reflective faces being separated by a width (w) of the resonant cavity 112. In some embodiments, a dielectric material, such as a biological material, liquid medicine, biological tissue and individual molecules with cancer properties, nanoscale thermal management or energy conversion material such as a nanowire and nanofilm, is positioned within the cavity such that a temperature of the dielectric material can be determined. Additional dielectrics may be used, such as dielectrics that possess a real part of the infrared refractive index that is less than the refractive index of the prism, and negligible infrared absorption. The walls 124-125 are configured to aid in retaining the dielectric material within the resonant cavity. Similarly, in some implementations, the prism 130 further aids in retaining the dielectric material. The substrate 120, the substrate surface 128, and/or surfaces of the walls 124-125 have surface phonon polariton properties that are used in determining a temperature. In some implementations, for example, the walls 124-125 may be formed of a gold or gold coating. For example, gold channel walls may be formed and/or positioned between the substrate 120 and the prism 130.

The light source 114 is positioned proximate the optical resonant cavity 112 and is configured to direct light toward the resonant cavity 112, and typically toward the prism-resonant cavity interface 132. Further, the light source 114 is typically positioned to direct light to and/or at the prism-resonant cavity interface 132 such that one or more evanescent waves induced from the light is guided into the resonant cavity that has the surface phonon polariton properties.

The light detector 116 is also positioned proximate to the resonant cavity 112 and configured to detect at least a portion of reflected light from the prism-resonant cavity interface 132, and/or at least a portion of the reflected light is directed to the light detector. Information about the detected light is communicated from the light detector to the temperature calculator 118. The temperature calculator 118 utilizes this information in determining a quality factor of the resonant cavity. The quality factor is dependent on a temperature of the dielectric material and/or a variation of a temperature of the dielectric material. Accordingly, the temperature calculator is further configured to determine and/or calculate a temperature and/or a change in temperature of a dielectric material within the resonant cavity as a function of the quality factor of the resonant cavity.

In some embodiments, the temperature calculator 118 determines evanescent light coupling to one or more phonon polariton modes from the resonant cavity. The temperature calculator further calculates a quality factor (sometimes referred to as the "Q-factor") as a function of a frequency spectrum of at least one of the one or more phonon polariton modes and/or mode responses from the resonant cavity induced from the incident light. Based on the determined quality factor, the temperature calculator determines a temperature of a dielectric material within the resonant cavity 112 as a function of the quality factor. Some embodiments further calibrate the determined quality factor and/or the determined temperature of the dielectric material. In some implementations, the calibration takes into consideration one or more independent ambient temperature measurements and/or one or more quality factor assessments corresponding to one or more other additional resonant cavities having different cavity widths. Some embodiments include one or more temperature sensors 134 that can be configured to measure an environment or room temperature, a temperature of the substrate proximate the cavity, a temperature of the substrate a distance from the cavity, and/or other such sensors.

The temperature calculator can serve as a combination of 1) Fourier Transform Infra-Red spectrometer with Attenuated Total Internal Reflection (FTIR-ATR), 2) calibration, and a 3) temperature computation instrument. For the FTIR-ATR, the surface resonances including the surface phonon polariton response of a select material is measured. The calibration can rely on the determination of the quality factor, Q, using a resonant cavity with metal reflecting walls and micron to nanoscale widths and nanoscale depths or metal reflecting wall height. Calibration can include an equation of fit describing the dependence of the quality factor, Q, on width for multiple temperatures (e.g., three or more different temperatures). Three temperatures can be used for a minimum estimate of temperature resolution. The temperature computation uses the information for the quality factor, Q, dependence on width and temperature to be used in concert with the calibration information to compute the temperature. In cases where the resonant cavity is filled with a material other than air, the calibration is repeated as described above using the new material filled cavity. In some instances, calibration includes macroscale environmental control and phononic/polaritonic referencing dictated by a given polar material substrate. Consequently, temperature measurements at the microscale follow: the thermometer measure of room temperature and/or temperature of an associated solvent at room temperature (e.g., in beaker near the measurement location). Quality factor determination can be performed for a prescribed set of resonance cavity widths ranging from phonon-polariton propagation distances to larger widths to establish a characteristic Q vs. T curve for a given choice substrate. By result of the FTIR-ATR and calibration above, fluids of different dielectric quality may be implanted in each resonant cavity of variable width. A single width can be used and compared to the characteristic Q(T) curve but for greater reliability, widths with set fluid may be measured with an emphasis on at least two resonant widths to determine the relative constants for the same equilibrium or reference temperature, $T_o$. If $Q=A\ w^{-\alpha}$ with w=width, then for two measured values of $Q_1$ and $Q_2$ for widths $w_1$ and $w_2$, the equation $(Q_1/Q_2)=(w_1/w_2)^{-\alpha}$ a determines a and subsequently the constant, A.

Figure 2:
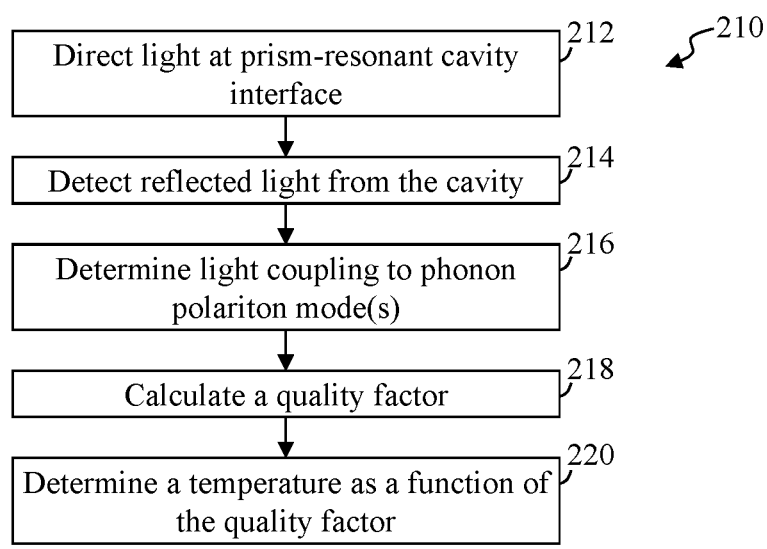
FIG. 2 illustrates a simplified flow diagram of a process of determining and/or sensing temperature, in accordance with some embodiments.

FIG. 2 illustrates a simplified flow diagram of a process 210 of determining and/or sensing temperature, in accordance with some embodiments. In step 212, light from the light source 114 is directed to the prism-resonant cavity interface 132. In some embodiments, the light source 114 provides light in the infrared and/or near infrared light spectrum. Some embodiments additionally or alternatively provide a p-polarized light (e.g., an infrared p-polarized light). The light source can generate and/or direct p-polarized infrared light toward an interface with an evanescent field injected into the resonant cavity.

As such, the p-polarized infrared light is directed to the prism-resonant cavity interface. Further, the light is directed at the interface to achieve at least partial reflection at the prism-resonant cavity interface 132, which can pump the optical phonon modes in the cavity. The resonant cavity is configured such that some or all of the evanescent field and/or wave(s) resulting from beam frustration at the prism-dielectric interface couples to optical phonon resonance modes localized within the resonant cavity, and in some instances at the dielectric-substrate surface interface. Further, in some implementations, the resonant cavity is configured to exhibit, in response to polarized light directed into the resonant cavity, surface phonon polariton excitation of the substrate that is dependent on a temperature of the dielectric material.

In step 214, the light that is reflected in response to the light being directed to the prism-resonant cavity interface is detected by the light detector 116. In step 216, evanescent light coupling to one or more phonon polariton modes from the resonant cavity is determined based on the detected reflected light. In step 218, a quality factor is calculated as a function of a frequency spectrum of at least one of the one or more phonon polariton modes. In some embodiments, the temperature calculator, in calculating the quality factor, is configured to calculate the quality factor as a function of the frequency spectrum of the surface phonon polariton modes response from the resonant cavity induced from the p-polarized infrared light. In step 220, a temperature of a dielectric material within the resonant cavity is determined as a function of the quality factor. Some embodiments further calibrate the temperature measurement system 110 and/or the determined temperature. The calibration, in some instances, is dependent on ambient temperature data obtained from one or more sensors. For example, temperature data corresponding to one or more ambient temperatures external to the resonant cavity can be determined, and the determined temperature of the dielectric material can be calibrated as a function of the temperature data corresponding to the one or more ambient temperatures. Additionally or alternatively, some embodiments assess quality factors determined from one or more additional resonant cavities. Further, one or more of the additional resonant cavities may have different physical dimensions than the first resonant cavity (e.g., different widths, w).

The calibration, in some embodiments, includes macroscale environmental control and phononic and/or polaritonic referencing, which can be dependent on and/or dictated by a given polar material substrate. For example, some embodiments measure an ambient temperature (e.g., room and/or lab temperature), such as through the measurement of a sample liquid or solvent positioned near or adjacent the location where nanoscale temperature measurements are being performed. Quality factors can be determined for a prescribed set of resonance cavities having different widths ranging from phonon-polariton propagation distances to larger widths. Using the determined quality factors, Q, a characteristic quality factor versus temperature curve can be determined for a given selected cavity.

Using the determined ambient temperature and the determined Q(T) curve, different dielectric materials having different dielectric quality (e.g., different liquid and/or solid dielectric materials) may be implanted in one or more resonant cavities, and often in multiple resonant cavities of variable width. The quality factor determined in each of the one or more resonant cavities can be evaluated relative to the Q(T) curve and/or each other. Again, one or more resonant cavities of a single width can be used and compared to the characteristic Q(T) curve; however, many embodiments achieve greater reliability when resonant cavities of varying widths are measured with an emphasis on at least two resonant widths to determine the relative constants for the same temperature, T. Defining $Q=Aw^{-\alpha}$ with w=width, then for two measured quality factor values of $Q_1$ and $Q_2$ for resonant cavity widths $w_1$ and $w_2$, the equation $(Q_1/Q_2)=(w_1/w_2)^{-\alpha}$ determines $\alpha$ and subsequently the constant, A, in calibrating the temperature measurement system 110 and/or the determined temperatures.

Figure 3:
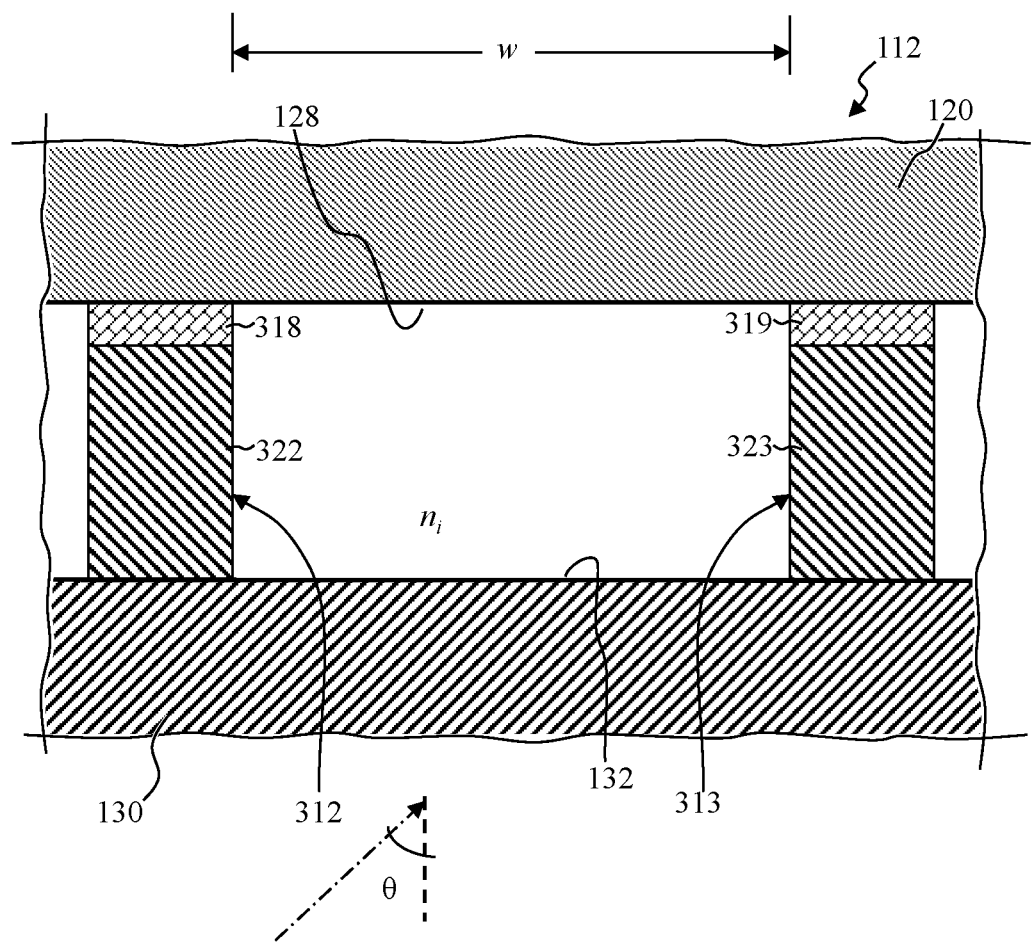
FIG. 3 shows a simplified, enlarged cross-sectional view of an exemplary resonant cavity, in accordance with some embodiments.

FIG. 3 shows a simplified, enlarged cross-sectional view of an exemplary resonant cavity 112 in accordance with some embodiments. As described above, the resonant cavity 112 includes walls 124-125 formed on or within the substrate 120 and defining the width (w) of the cavity. Further, each wall includes a reflective surface or face 312-313 separated from each other by the width of the resonant cavity. The reflective surfaces are further positioned opposite each other and oriented inward to the cavity. The walls are typically further configured to aid in retaining a dielectric material within the resonant cavity.

The prism 130 is positioned adjacent to and typically against at least the walls 124-125 enclosing the cavity. In some embodiments, the prism is formed from a crystal, lens, or other such structure of the light source 114, the light detector 116, or a combination of the light source and the light detector. For example, in some implementations, the light source and the light detector are integrated within a system, such as an infrared spectrometer, a Fourier Transform Infrared Spectrometer with attenuated total reflection (FTIR-ATR), or other such measurement system. Similarly, the temperature calculator may be integrated and/or cooperated with one or both of the light source and the light detector. Further, in some embodiments, the prism 130 is a prism, lens, diamond, crystal, or the like of the measurement system, such as but not limited to a lens of a FTIR-ATR, a diamond of a FTIR-ATR, a photonic crystal, or the like.

Additionally, in some embodiments, the resonant cavity 112 is formed through wafer processing or similar techniques to form the resonant cavity and/or walls in and/or on the substrate. For example, some embodiments implement microfabrication to pattern the cavity and/or deposit material to form the walls 124-125. In certain approaches, the resonant cavity is formed on and/or in a silicon wafer (e.g., a silicon dioxide ($SiO_2$), such as a 500 μm thick $SiO_2$ wafer). Other substrates may be used, such as gallium nitride (GaN), silicon carbide (SiC), and/or other such materials or combinations of such materials. Many of the examples above and below are presented in relation to a silicon dioxide substrate. Other embodiments, however, can utilize other substrates that exhibit sufficient surface phonon polariton properties, such as but not limited to gallium nitride and silicon carbide. Such substrates may be used with high power semiconductors. The performance of high power density devices can be strongly limited by heat transfer. Managing heat transfer can be crucial to developing and implementing high power density, semiconductor based devices. Accordingly, the temperature sensing and/or determination can be critical in the processing and development of such high power density devices, and other such applications. Most crystalline or polycrystalline materials comprised of infrared active, molecular electric dipoles perpendicular to the interface may be used. Other examples include aluminum oxide ($AlO_2$) and zirconium oxide ($ZrO_2$).

In some embodiments, the walls are formed from a metal and/or a reflective layer of metal is formed on the walls. As a non-limiting example, wafer processing and/or microfabrication processes form walls of chromium and/or form a layer of chromium on the walls to create the reflective surfaces 312-313. In other embodiments, the walls are formed of gold or a gold alloy and/or a layer of gold or gold alloy is formed on the walls to create the reflective surfaces. Further, some embodiments utilize metals with a reflectance of 99% or greater for normal incident infrared light may be used, including gold, silver, and copper. Further, the walls in some embodiments are formed comprising two or more portions that are formed from different materials. As an example, the opposing walls may comprise a first portion or base 318-319 of the walls formed from a first substance that readily bonds with silicon dioxide (e.g., chromium) Fabrication specific involve the details of metal-to-polar substrate adhesion, and/or metal layer deposition. Other materials such as, but not limited to, silicon dioxide ($SiO_2$), silicon carbide (SiC), zinc oxide (ZnO), gallium nitride (GaN), and other such materials, could serve as polar substrates with gold-chromium, silver, or copper, 99% IR reflective metal cavity walls, and with a second portion or extension 322-323 of the wall being formed from gold bonded to at least the first portion of the wall. The second portion 322-323 is secured, bonded, soldered, or the like with and extends from the first portion. At least the second portion 322-323 of the wall includes the reflective surface 312 and 313 (e.g., metallic reflective surfaces).

The dimensions of the resonant cavity and/or the walls may vary depending on many factors, such as but not limited to a dielectric material for which temperature is to be measured, material forming the substrate, material or materials forming the walls, the incident light, expected temperature ranges, and/or other such factors. The chosen cavity width, w, may depend on the SPhP propagation length, $l_P$. The upper limit on the w is determined to be when the ratio of reflection rate to loss rate, begins to exceed that of the other infrared cavity waves, where the ratio is directly proportional to the Q-factor. The SPhP Q-factor begins to grow larger than the Q-factor for other infrared cavity waves when the cavity width is about 10 times the SPhP propagation length. Cavity height (i.e. the height of the metal reflecting walls) depends on how deep the evanescent wave can penetrate the cavity to couple to substrate lattice vibrations. This depth is called the evanescent wave penetration depth, $\delta_p$, which depends on the refractive index of the dielectric, $n_i$, and prism (e.g., $n_i$ and $n_{diamond}$, the refractive index of the dielectric and prism respectively). For dielectrics with $n_i < n_{diamond}$, evanescent wave penetration depth $\delta_p$ is about 2 microns, which sets an upper limit on the cavity height. There is typically no upper limit on length, however in some embodiments, length can be on the order of the width w. In some embodiments, the resonant cavity 112 is a microscale or nanoscale resonant cavity having dimensions that are less than tens of millimeters, and in some instances hundreds of micrometers or less. In some implementations, the one or more resonant cavities are formed in and/or on a substrate 120, with cavity depths that are typically less than about 1.0 µm, and with widths that can vary significantly, such as from widths much greater (e.g., about 2000 µm) than the surface-phonon polariton propagation length (which is, for example, about 10-100 µm) to distances that are comparable to the surface-phonon polariton propagation length (e.g., about 10 µm or greater).

For example, some embodiments form the resonant cavity 112 in or on a silicon dioxide wafer and form a first portion of a wall with a height of about 10 nm of chromium and a second portion of the wall with a second height of about 240 nm of gold providing a resonant cavity depth of about 250 nm. A length of the resonant cavity may vary depending on an implementation. In some embodiments, the length may be greater than about 200 nm, while in some embodiments, the length may be 1 mm or more. Similarly, the formed width, w, can depend on one or more factors, such as those described above and/or other such factors. Still further, some embodiments form multiple resonant cavities with two or more of the resonant cavities having different widths, which may be used in calibration and/or confirmation of determined temperatures.

The cavity height may be limited in that substrate molecular electric dipoles are not neutralized, or damped out. Thus the lower limit on the cavity height may in some instances be on the order of the substrate molecular dipole radius, which may be on the order of $10^{-10}$ m to $10^{-9}$ m (nanoscale). Cavity width may be "sub-diffraction limited". This limits the width to $w/\lambda \ll 1$ where $\lambda$ is the wavelength of the light. When the sub-diffraction limit is reached, the SPhP mode can no longer be contained in the cavity at rates necessary to sustain the Q factor enhancement.

As described above, the prism 130 is further cooperated with the cavity. Again, in some embodiments, the prism 130 may be a part of the light source 114, light detector 116, and/or a system including two or more of the light source, light detector, and/or the temperature calculator 118. For example, in some embodiments, the prism 130 may be formed at least in part by the cavity formed by attaching the substrate 120, and walls 124-125 with an FTIR-ATR spectrometer prism 130 (e.g., diamond, ZnSe crystal, etc.) to form a resonant cavity, such as the resonant cavities 112 similar to those depicted in the cross-sectional views in FIGS. 1 and 3.

Further, the resonant cavity 112 provides a longitudinal and transverse optical phonon cavity formed by a channel having a length, l (not illustrated, oriented into and out of the plane of the page depicted in FIGS. 1 and 3) such as 1 mm, and the width, w, with walls 124, 125 (e.g., gold/Cr walls), a silicon dioxide substrate (sometimes positioned as a top) and a diamond as the prism 130 (sometimes positioned as a bottom). The resonant cavity is filled with the dielectric material having a refractive index, $n_i$.

The light source 114 is positioned relative to and/or proximate the cavity such that incident light, ω, from the light source is directed to impinge on the prism-resonant cavity interface 132. Further, the light directed by the light source may be polarized, which may pump the optical phonon modes in the resonant cavity 112. Further, the light, ω, is typically directed at an incident angle θ to an axis perpendicular to a plane defined by the prism-dielectric interface 132 and/or the substrate surface 128. The incident angle θ is further typically selected to achieve at least some reflection of the light by the prism-resonant cavity interface, and in some instances the incident angle is implemented to achieve a total internal reflection (TIR). For example, in some embodiments, an incident angle θ=45° is selected such that an incident beam is totally reflected at the prism-resonant cavity interface when the refractive index of the prism 130, $n_{prism}$, is greater than a refraction index, $n_i$, of the dielectric and/or the cavity or channel region. The reflection of the light (e.g., with $n_i < n_{prism}$ and the incident angle θ equal to about 45°) can induce evanescent waves at the diamond/dielectric interface that extend across the gap to support optical phonon modes at the silicon dioxide substrate-dielectric interface. Further, the evanescent wave, waves, and/or field resulting from the beam frustration at the prism-resonant cavity interface (e.g., the prism-dielectric interface) couple to one or more optical phonon resonance modes of the resonant cavity. In some implementations, the evanescent wave couples to one or more optical phonon resonance modes localized at the dielectric-substrate interface.

Furthermore, the reflective surfaces 312-313 of the walls 124-125 can be formed to be reflective to one or more optical phonon modes corresponding to the bandwidth of the light directed by the light source 114. For example, the reflective surface can be configured to be highly reflective to infrared optical phonon modes, which can result in light field confinement between the interfaces of the surfaces, substrate, and prism (e.g., light field confinement between the surfaces of the gold, silicon dioxide, and diamond interfaces). Still further, as described above, the width (w) of the resonant cavity or cavities can vary.

For example, one or more longitudinal and transverse optical phonon resonant cavities can be formed by separate resonant cavities with different widths (w) defined by the reflective walls (e.g., gold and chromium walls) and a substrate (e.g., a silicon dioxide substrate). A prism closes the cavity (e.g., a diamond bottom). The cavity can be filled with a dielectric material having a refractive index, $n_i$. Light is directed at the prism-resonant cavity interface 132, which is also the prism-dielectric interface. For example, a p-polarized and/or s-polarized infrared light, ω, is directed to impinge on a diamond-dielectric interface at an incident angle θ. In those instances where the refractive index of the dielectric material (n) is less than the refractive index (e.g., $n_{diamond}$) of the prism (e.g., $n_i < n_{diamond}$), the incident angle can be set at about θ=45°. Evanescent waves at the prism-dielectric interface typically extend across the gap to support optical phonon modes at the substrate-dielectric interface (e.g., $SiO_2$/dielectric interface). The resulting $SiO_2$ resonance modes are confined within the resonant cavity by the walls 124, 125.

Typically, the phononic resonances are temperature dependent. Accordingly, some embodiments utilize the phononic resonances in temperature sensing and/or determining temperature at nanoscales (e.g., less than thousands of nanometers and typically less than hundreds of nanometers). Accordingly, some embodiments provide phononic thermosensors. Some embodiments utilize a quality factor of one or more resonant cavities, which typically vary with optical width, and by taking advantage of the relationship of the optical width to dielectric thermo-optical properties, determine and/or estimate quality factor dependence on temperature.

In evaluating and/or analyzing phonon polariton modes, some embodiments perform an analysis on at least the transverse optical (TO) phonons modes that can be sustained within one or more frequency ranges. For example, some implementations evaluate the transverse optical modes that can be sustained in the frequency range between $\omega_a$=864 cm$^{-1}$ and $\omega_b$=1241 cm$^{-1}$, wherein the TO modes within this region include the transverse Si—O—Si vibrations at 1064 cm$^{-1}$ and 1160 cm$^{-1}$, and the Si—OH stretch at 960 cm$^{-1}$. In some embodiments, such as some embodiments that include a silicon dioxide substrate with an infrared incident light, it is determined that the coupled light-lattice vibrations at 1160 cm$^{-1}$ correspond with at least one of the surface phonon polariton modes. It has been determined that these modes are possible sources for spectrally selective infrared emitters.

In operation, the light detector 116 detects at least a portion of reflected light from the prism-resonant cavity interface 132, and/or at least a portion of the reflected light is directed to the light detector. The reflected light intensity is reduced in regions of the spectra at, and near, the SPhP coupling frequency. The reflected light intensity spectra is communicated from the light detector to the temperature calculator 118. In some embodiments, the light detector may perform some processing and/or analysis of the detected light. In other embodiments, the temperature calculator may perform some or all of the analysis and/or processing of the detected light. The processing of the detected light may include spectra ranges and/or evaluations, intensity identification and/or evaluation, and/or other such information.

In some embodiments, the light detector 116 and/or the temperature calculator 118 detect and/or identify the light coupling to one or more phonon modes, such as identifying light coupling to the transverse optical phonon modes. For example, in some instances, the light coupling to the transverse optical phonon modes are detected as dips in reflection spectra. Using the detected reflected light and the evaluation of the reflected light a quality factor of the resonant cavity can be determined. As described further below, and in accordance with some embodiments, it is identified that the quality factor corresponding to at least one or more phonon modes of the resonant cavities typically comply with and/or obey an inverse power law dependence on a width of the resonant cavity. Further, the optical path length is related to the width of the resonant cavity, and to a temperature using a thermo-optical coefficient. Accordingly, the quality factor has a temperature dependence. Additionally, some embodiments relate the optical width to the dielectric thermo-optical properties to obtain quality factor dependence and/or an estimate of quality factor dependence on temperature. The temperature dependence of the quality factor is a practical result that describes the energy dissipative behavior of one or both mechanically and optically responsive systems.

Figure 4:
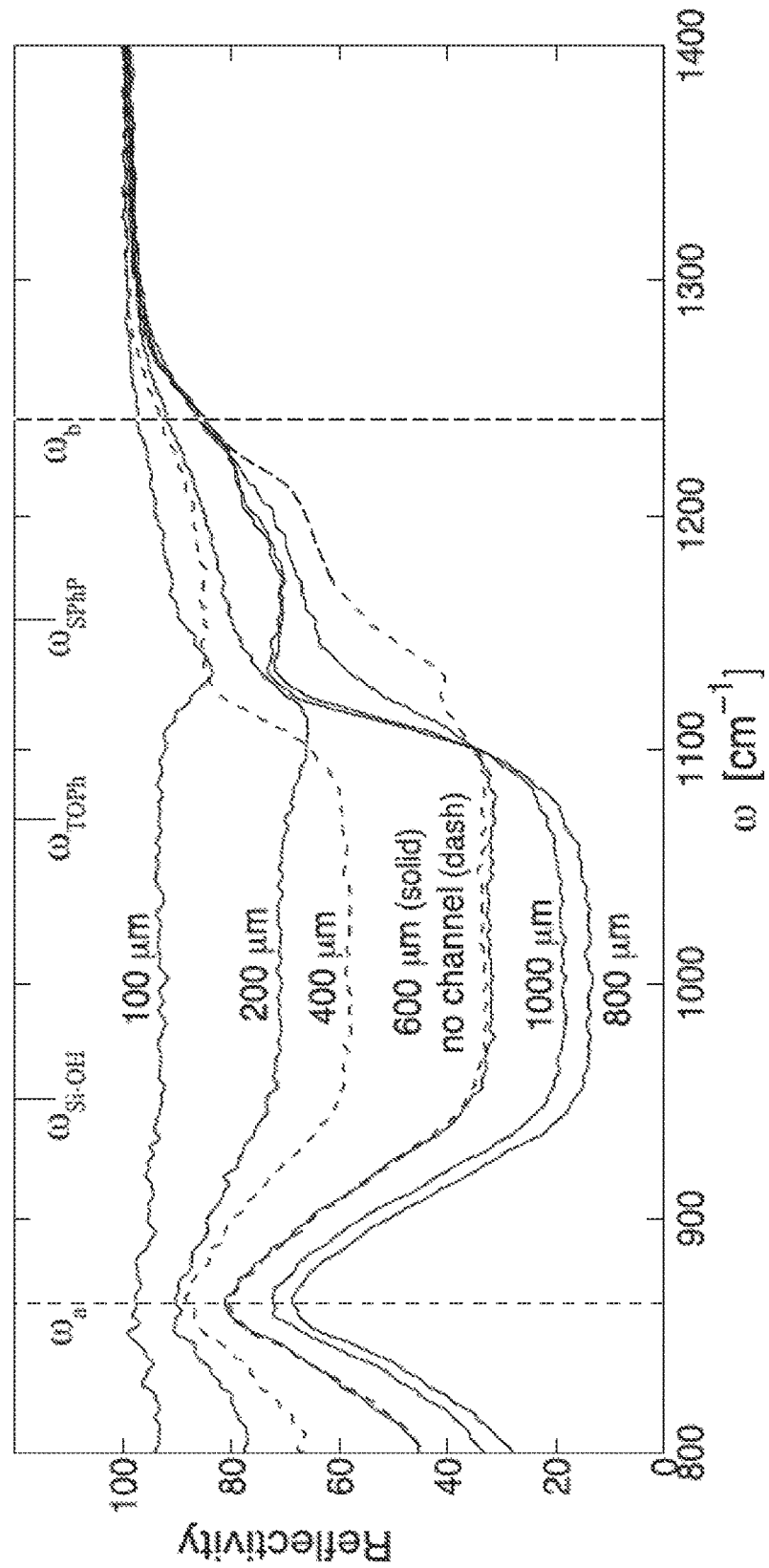
FIG. 4 shows a graphical representation of an analysis over a bandwidth of an exemplary reflection spectra from a p-polarized infrared light directed at a prism-resonant cavity interface, in accordance with some embodiments.

FIG. 4 shows a graphical representation of an analysis over a bandwidth of an exemplary reflection spectra from a p-polarized infrared light directed at a prism-resonant cavity interface, in accordance with some embodiments. In this representation, the reflection spectra is based on an analysis of light reflected from the prism-resonant cavity interface 132 in response to p-polarized infrared light directed at the prism-resonant cavity interface of a resonant cavity, which may be similar to that depicted in FIG. 3, having a silicon dioxide substrate, reflective surfaces 312-314 and/or walls that are gold over at least a part of a length or depth of the walls, and a diamond prism 130. The graphical representation in FIG. 4 further shows the spectral curves for different resonant cavities having different widths w of 100 μm, 200 μm, 400 μm, 600 μm, 800 μm, and 1000 μm, labeled in FIG. 4 accordingly.

In some embodiments, a quality factor of the resonant cavity 112 is determined and/or calculated as a function of a determined full-width-half-maximum, $\Delta\omega$, and a dip minimum frequency location, $\omega_0$, of dips in the reflection spectra and/or frequency pulse of the reflected light within a frequency range of interest (graphically illustrated in FIG. 4 by the vertical dashed lines at $\omega_a$ and $\omega_b$). For example, the light detector and/or the temperature calculator can detect and/or identify light coupling to one or more transverse optical phonon modes as dips in the reflection spectra. In some instances, an FTIR-ATR is employed in detecting and/or identifying the light coupling to the one or more transverse optical modes. One or both of the full-width-half-maximum, $\Delta\omega$, and the dip minimum location, $\omega_0$, parameters are often dependent on the materials forming the resonant cavity, such as the material of the substrate establishing the dielectric-substrate interface. In determining and/or defining the full-width-half-max of the frequency pulse $\Delta\omega$, some embodiments note that the dip minimum $\omega_0$ of the frequency pulse is the spectral location of $R^{a-b}{}_{min}$, which is a detected minimum reflectivity (e.g., minimum ATR reflectivity) within the frequency range of interest between $\omega_a$ and $\omega_b$. For example, when considering a resonant cavity having a substrate surface of silicon dioxide, the frequency range may be defined as the range between $\omega_a$=864 cm$^{-1}$ and $\omega_b$=1241 cm$^{-1}$ within which at least some of the transverse optical (TO) phonon modes can be sustained. Accordingly, in some embodiments, the full-width-half-max of the frequency pulse is defined by $$\Delta\omega = \omega_{+0.5\ min} - \omega_{-0.5\ min},$$

where $\omega_{+0.5\ min}$ is the spectral location of A=0.5* $(1-R^{a-b}{}_{min})$, which in FIG. 4 is to right of $R^{a-b}{}_{min}$, and $\omega_{-0.5\ min}$ is the spectral location of A=0.5*$(1-R^{a-b}{}_{min})$, which in FIG. 4 is to the left. The full-width-half-max of the frequency pulse $\Delta\omega$ and the dip minimum $\omega_0$ of the frequency pulse can be used, in some embodiments, to determine the quality factor of the cavity and/or the quartz optical phonon surface resonances confined within the cavity. For example, some embodiments calculate the quality factor as a function of a ratio of the dip in minimum frequency ($\omega_0$) and the full-width-half-maximum frequency range ($\Delta\omega$).

Further, as introduced above, the quality factor is dependent on the temperature. It is further noted that the optical path length between the cavity walls is also related to the temperature. The optical path is defined for waves traveling along the prism-dielectric and/or substrate-dielectric interfaces. This path is fixed with respect to refractive index and should change with allowable standing waves. Thus, the propagation vector, k, changes inversely with the width of the resonant cavity. In some implementations, the optical path length can be defined by $w_{opt} = n_i w$, where both the refractive index ($n_i$) and the width (w) may depend on temperature.

Figure 5:
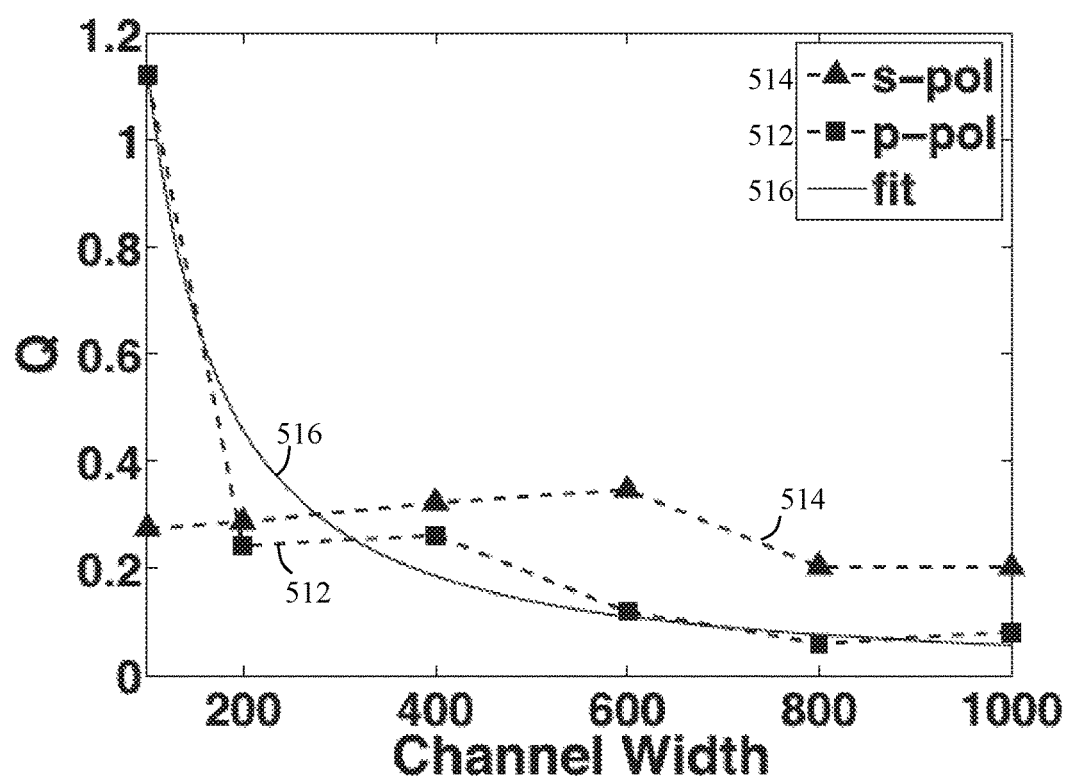
FIG. 5 shows a graphical representation of determined variations in quality factors of resonant cavities as width of the resonant cavities vary and relative to both p-polarized infrared incident light and s-polarized infrared incident light over the a frequency range, in accordance with some embodiments.

As demonstrated in FIG. 5, the quality factor Q increases at smaller widths w, at least to a threshold width. FIG. 5 shows a graphical representation of determined variation in quality factors of resonant cavities as width of the resonant cavities vary and relative to both p-polarized infrared incident light 512 and s-polarized infrared incident light 514 over the same frequency range $\omega_a$ to $\geq_b$ as depicted in FIG. 4, in accordance with some embodiments. It is noted that the dramatic increase in the quality factor within this frequency range is relevant to the p-polarization data. This observation suggests that long-range transverse vibrations coupled to the light fields and the surface phonon polaritons (SPhP) are responsible for the quality factor variations (e.g., increases in quality factor as the width decreases, at least to threshold size) because SPhP are p-polarized phenomena.

Figure 6:
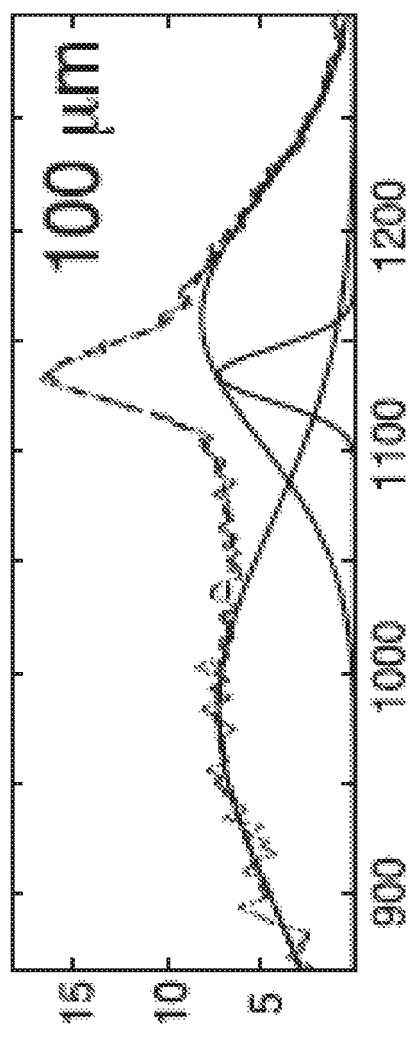
FIGS. 6 and 7 each show graphical representations of examples of 3-peak Gaussian fittings for spectra of sample resonant cavity widths, in accordance with some embodiments.
Figure 7:
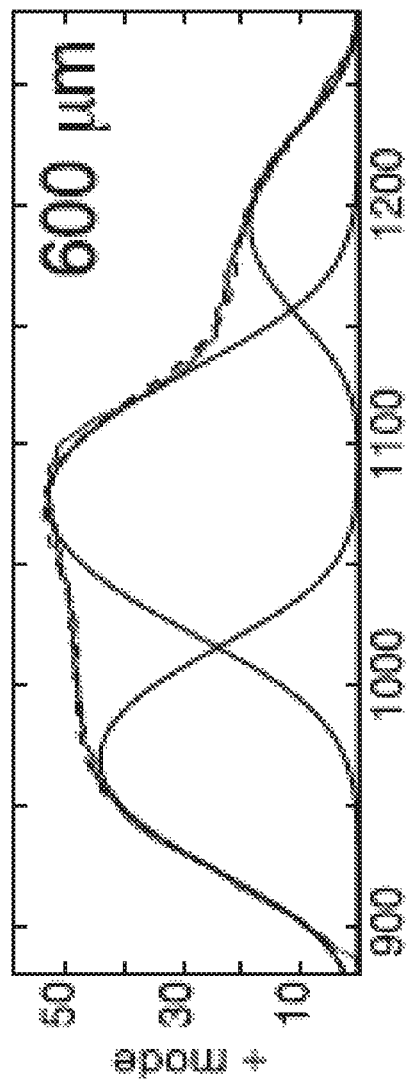

A summation of Gaussian functions can be applied in evaluating the contribution of individual vibrational modes on the quality factor variations with channel width, and deconvolve the incident and/or detected spectra corresponding to multiple different resonant cavity widths. Curve fitting can be applied (e.g., using MATLAB curve fitting algorithm). FIGS. 6 and 7 each show graphical representations of examples of 3-peak Gaussian fittings for spectra of sample resonant cavity widths, w=100 μm and 600 μm, respectively, in accordance with some embodiments. In approaching a peak fitting, optical transverse vibrational modes are considered corresponding, for example with the substrate, such as optical transverse vibrational modes associated with silicon dioxide: $\omega_{Si-OH}$=960 cm$^{-1}$, $\omega_{TOPh}$=1065 cm$^{-1}$, and $\omega_{SPhP}$=1160 cm$^{-1}$. Using the Gaussian fitting, the spectral location of the Gaussian curve peak, co, most closely related to the transverse optical modes (e.g., i=Si—OH, TOPh, and SPhP), can be determined. The full-width-half-max of the frequency pulse $\Delta\omega_i$ can be calculated as a full-width-half-max of each Gaussian associated with each mode with index, i. Using the determined peak frequency, $\omega_i$ and the full-width-half-max $\Delta\omega_i$, the quality factor for various cavity widths can be calculated in accordance with $Q_i=\omega_i/\Delta\omega_i$.

Figure 8:
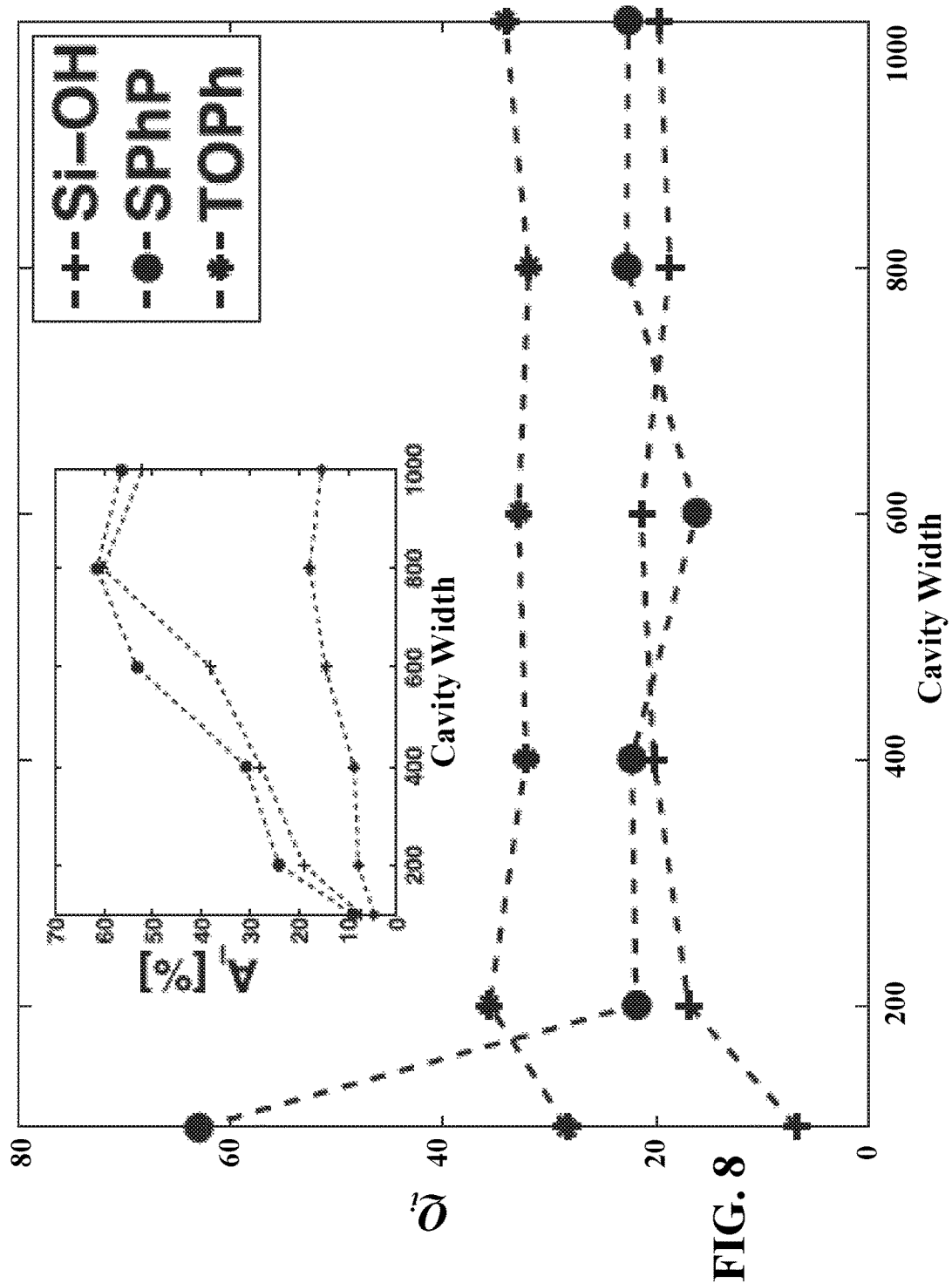
FIG. 8 shows a graphical representation of the quality factor of each relevant mode relative to changes in the width of the resonant cavities, in accordance with some embodiments.

FIG. 8 shows a graphical representation of the quality factor $Q_i$ of each relevant mode (in this example, for silicon dioxide substrate i=Si—OH, TOPh, and SPhP) relative to changes in the width of the resonant cavities, in accordance with some embodiments. As seen from FIG. 8, the plotted quality factors ($Q_i=\omega_i/\Delta\omega_i$) illustrate that while the Si—OH and TOPh vibrations lose energy as the resonant cavity width w is decreased, the SPhP mode has a quality factor that increases as the resonant cavity width w is reduced, at least as the width approaches a minimum threshold, e.g., a width that is comparable to the surface-phonon polariton propagation length. It has been determined experimentally and theoretically that the propagation length for SPIT, $l_{p,SPhP}$, in SiO$_2$ is about 11 microns. As the cavity width approaches $l_{p,SPhP}$, that is w $l_{p,SPhP}$ a Q factor enhancement is seen. The minimum cavity width is given by the sub-diffraction limit, which limits the width to $$\frac{w}{\lambda} \ll 1$$

where λ is the wavelength of the light. When the sub-diffraction limit is reached, the SPhP mode can no longer be contained in the cavity at rates necessary to sustain the Q factor enhancement.

Further, some embodiments consider a Gaussian peak height to estimate a change in absorptivity A=(1−R) for each Gaussian peak i for varying resonant cavity width w. FIG. 8 further includes an inset that graphically illustrates exemplary absorptivity relative to cavity width for three resonant modes (i=Si—OH, TOPh, and SPhP), in accordance with some embodiments. The cavity absorptivity decreases for all three vibrational modes (i=Si—OH, TOPh, and SPhP) as the cavity width w decreases.

Because there is a strong suggestion that the SPhP transverse optical mode is responsible for the increase in the quality factor, at least with respect to the silicon dioxide substrate and p-polarized infrared light, the dependence of the transverse optical mode lifetime on cavity width w can be estimated by performing an exponential fit 516 of the quality factor versus width of the resonant cavity data as:

$$Q=Aw^{-\alpha}, \quad\quad\quad \text{EQ. (1)}$$

which is also plotted in FIG. 5 for α=1.3, and A=450. In some embodiments, the cavity resonator establishes coupled light-lattice modes that propagate along the substrate interface and are long lived when the width of the cavity is sufficiently small (i.e., the cavity walls are narrow enough) so that the ratio of wave energy reflected by the metal walls to SPhP losses from the cavity increases significantly. A cavity width is sufficiently small when the width is around 10 times the SPhP propagation length, $l_{p,SPhP}$, or less. Further, in some instances, when the width of a cavity is sufficiently large, measured effects do not significantly differ from when no cavity is present. A cavity width is sufficiently large when the width is much greater than the SPhP propagation length, $l_{p,SPhP}$, by a factor of 100 or more. Typically, as the width of the resonant cavity is reduced to around 10 times $l_{p,SPhP}$, or less, the cavity metal walls reflect multiple evanescent waves associated with the beam and an expected enhancement should occur. In some embodiments, resonant cavity quality factors are expressed by ratios of polynomials for fitting purposes. However, in some instances, the expected increase at diminished cavity width may be qualitatively described by an exponential fit and provides an estimate of how long-lived the phonon-polariton or other excitation influences would be as w is decreased. For example, some embodiments use an interpretation that the quality factor estimates the number of cycles needed for the system to substantially lose about 99.8% of its energy.

Some embodiments may further expand the spectral range to include an evaluation of the characteristic transverse optical phonon peak of silicon dioxide at about 795 cm$^{-1}$ and perform an iterative Gaussian fit for spectra across multiple different resonant cavity widths, w. For example, some embodiments perform the iterative Gaussian fit (e.g., employing Igor Pro software, from WaveMetrics). FIG. 9 shows a Table listing determined peaks and their standard deviations, in accordance with some embodiments. The reference peaks, as specified in some literature for silicon dioxide, are listed on top for each column.

As introduced above, in determining the quality factor dependence on temperature, it was also identified that the optical path length between the cavity walls is also related to the temperature. The optical path is defined for waves traveling along one or more of the substrate-dielectric and/or prism-dielectric interfaces. The optical path is fixed with respect to refractive index and can change per material variation. For the supported standing waves within the cavity, the optical path is directly proportional to both the refraction index and the cavity width. Thus, the propagation vector, k, changes inversely with the width of the resonant cavity or geometric boundary conditions. Additionally, each spectrum is typically width dependent. Further consideration, confirmation, and/or calibration may be considered in view of results obtained relative to fixed cavity width and varied temperature as well as the consideration of different widths to include variations in the refractive index with temperature. This is ultimately realized by the optical path length, $w_{opt}=n_i w$, where the refractive index ($n_i$) and resonant cavity width (w) can depend on temperature. In some instances, with liquid dielectric materials additional variations may occur for large versus small widths when considering non-equilibrium or quasi-equilibrium conditions where the diffusive freedom of particles may play a role.

For liquids, the differential optical path length, $dw_{opt}$, is related to the thermo-optical coefficient, $dn/dT$, and the physical length, $w_0$, by:

$$dw_{opt,liq} = w_o \frac{dn_i}{dT} dT, \quad \text{EQ. (2)}$$

while for solids:

$$dw_{opt,sol} = \left[ w_o \frac{dn_i}{dT} + \Delta_\alpha + \Delta_q \right] dT, \quad \text{EQ. (3)}$$

where $\Delta_\alpha$ accounts for the optical effects of thermal expansion and the $\Delta_q$ term characterizes the thermal stresses. The physical length is viewed as based on the surface structure of the polar substrate. For example, with a lattice type structure, the physical length, $w_o$, corresponds to the characteristic lattice spacing. In accordance with equations (2) and (3), the form of the differential optical path can be defined by:

$$dw_{opt}=CdT,$$

where C is a constant and typically a constant over a predefined range of temperatures from the known equilibrium temperature, when $dn_i/dT$, $\Delta_\alpha$, and $\Delta_q$ do not vary with temperature. In some instances, for example, the optical path approximation is valid over small temperature ranges around an equilibrium temperature, $T_0$ (e.g., $T_0 \pm 10^{-5}$ K to $T_0 \pm 10^{-2}$ K). The use of the resonant cavities in measuring nanoscale temperatures, however, is not restricted to variations from room temperature. Rather, the temperature determination and/or the determination of a variation in temperature can be utilized with a wide range of equilibrium temperatures and the detection of changes from a given equilibrium temperature.

Integrating the differential optical path $dw_{opt}$ to a temperature T, which is typically a relatively small temperature variation (e.g., about a $10^{-5}$ to $10^{-2}$ degrees Kelvin change) from the equilibrium temperature, $T_0$, in accordance with:

$$\int_{w_{i,opt}}^{w_{opt}} dw = w_o \int_{T_0}^{T} CdT', \quad \text{EQ. (4)}$$

where a difference in path length can be defined by:

$$w_{opt}-w_{i,opt}=w_o C[T-T_0]. \quad \text{EQ. (5)}$$

Because $w_{i,opt}$ and $T_0$ are constants that can be arbitrarily chosen, the optical path length dependence on temperature can be defined, in accordance with some embodiments, as:

$$w_{opt}(T)=w_o CT. \quad \text{EQ. (6)}$$

In some embodiments, Equation (6) is applicable to liquid and solid dielectric materials for changes in temperature (T) from the equilibrium temperature, and typically relatively small changes of $+10^{-5}$ K to $+10^{-2}$ K in temperature from the equilibrium temperature. Because of the empirical influence of both the transverse optical phonon modes and the apparent phonon-polariton influence, the cavity width, w, can be used as an accurate estimation of an effective optical path length, $w_{opt}=w$. Again, as described above, the quality factor has a temperature dependence. Accordingly, in some embodiments, the quality factor, Q, can be rewritten to depend on temperature. Considering Equation (6) with Equation (1), in some embodiments, the quality factor variation with temperature may be written as:

$$Q=A^*(w_o CT)^{-\alpha}. \quad \text{EQ. (7)}$$

where A is a surface phonon-polariton resonant cavity specific constant, $w_o$ defines a known optical path length at a known equilibrium temperature, C is a constant over a predefined range of temperatures from the known equilibrium temperature, and $\alpha$ is a surface phonon-polariton resonant cavity specific scaling constant. For example, with a silicon dioxide substrate, gold/chromium based surface phonon-polariton resonant cavities, the quality factor can be defined as:

$$Q=450^*(w_o CT)^{-1.3}.$$

Accordingly, in some implementations, the temperature dependency of the quality factor can be approximated according to $Q \sim T^{-\alpha}$. When temperature measurements of any system in thermodynamic equilibrium are taken at different times, the observed temperatures will fluctuate above, or below, a mean temperature. The mean temperature depends on the system thermodynamic properties and temperature. The standard error, $s_e$, quantifies how large the observed temperature fluctuations will be, and thus sets a lower limit on how close any two different mean temperatures can be measured, where the "mean temperature" is the accurate representation of the equilibrium state. For a mean temperature in equilibrium state one, $T_{0,1}$, the smallest measurable higher equilibrium temperature will be $T_{0,2} = T_{0,1} + \Delta T_f$, where $\Delta T_f$, the fluctuation limited smallest difference, is defined by the standard error.

For example in low temperature systems, statistical mechanics accurately gives the standard error for thermal fluctuations away from the mean temperature value as $s_e = k_B T^2/(m_i c_p)$, where $m_i$ is the mass of dielectric in the cavity, and $c_p$ is the specific heat. In this case, the smallest $\Delta T$ required to achieve a 99% probability that the mean temperature is within the measurement range, is given by $\langle (\Delta T_f)^2 \rangle /s_e$ or $$\langle (\Delta T_f)^2 \rangle \frac{m_i c_p}{k_B T^2} = 0.99$$

However, there is also a lower limit on the smallest temperature change that can be utilized to experimentally determine $c_p$, and the other thermodynamic properties such as the volumetric coefficient of thermal expansion, and the constant C, which is defined by the second law of thermodynamics.

For a constant pressure process with reversible heating, the relationship between volume and temperature change are related to the dielectric material coefficient of thermal expansion, $\beta$. For a constant pressure process, $\beta$ is related to a materials temperature and volume by $$dV=V\beta dT$$

which, when compared to EQ. (2), for some cases, the constant C is equivalent to β, thus providing a thermodynamic basis for C as a material property. The C is determined by measuring temperature and volume at varying equilibrium states during constant pressure and reversible heating. The temperature variations during used to calculate C should be small enough that entropy generation is negligible (reversible).

Entropy generation by heat flow across a temperature difference, ΔT, is given by $$\dot{S}_{gen} = \dot{Q}\frac{\Delta T}{T^2}$$

$$\dot{S}_{gen} = \dot{Q}\frac{\Delta T}{T^2}$$

for the closed system, second law gives $$\dot{S}_{gen} = \dot{S}_2 - \dot{S}_1 - \int \frac{\delta \dot{Q}}{T} \geq 0$$

$$\frac{\dot{Q}\frac{\Delta T}{T^2}}{\int \frac{\delta \dot{Q}}{T}} = \frac{\dot{S}_2 - \dot{S}_1}{\int \frac{\delta \dot{Q}}{T}} - 1$$

So when $$\frac{\dot{Q}\frac{\Delta T}{T^2}}{\int \frac{\delta \dot{Q}}{T}} \ll 1$$

it can be expected that entropy generation approaches zero, and an accurate measure of thermodynamic properties is approached in this limit. In other words, the maximum temperature difference as dictated by the second law is $$\Delta T_{II} \ll \frac{T^2 \int \frac{\delta \dot{Q}}{T}}{\dot{Q}}$$

Thus the temperature differences are within the range $\Delta T_f$ and $\Delta T_{II}$. It is noted that $\Delta T_f$ is a measured property that depends additionally on the optical response of the prepared dielectric substrate. By analogy, reference to the known role of a thermometer's characteristic resistance can be considered in producing an accurate measure when probing temperature dependent magnetization.

Accordingly, some embodiments provide systems and methods of measuring temperature changes with nanoscale resolution through the use of the quality factor of optical surface phonon modes confined to a resonant cavity (e.g., a generally rectangular resonant cavity). Further, in some implementations, temperature dependence of the quality factor can be approximated as following $Q \sim T^{-\alpha}$, which is similar to a power rule that has been observed in other mechanical and acoustic resonance systems.

Figure 10:
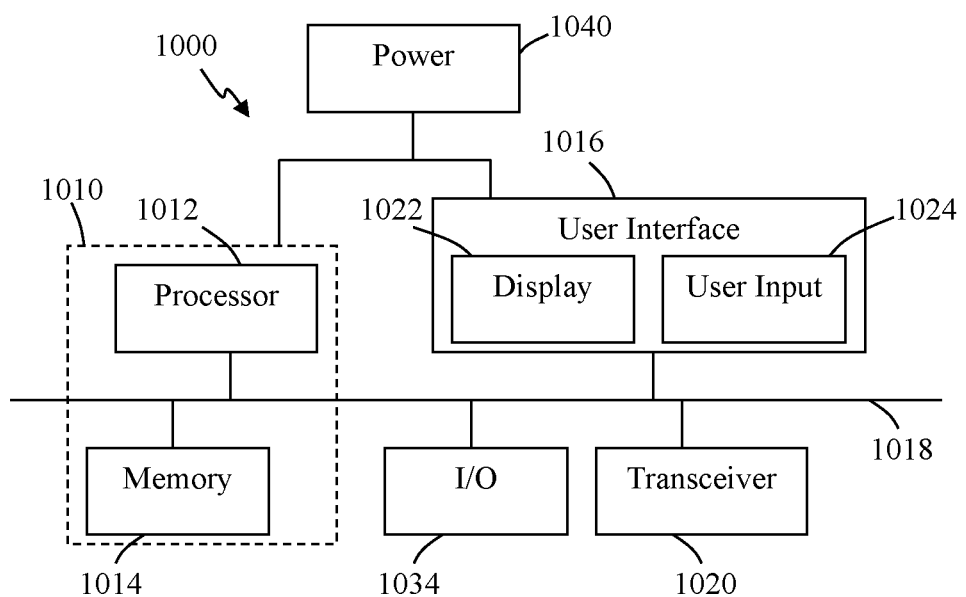
FIG. 10 illustrates an exemplary system for use in implementing methods, techniques, devices, apparatuses, systems, servers, sources and the like in providing user interactive virtual environments in accordance with some embodiments.

The methods, techniques, systems, detectors, calculators, devices, sources and the like described herein may be utilized, implemented and/or run on many different types of devices and/or systems. Referring to FIG. 10, there is illustrated a system 1000 that may be used for any such implementations, in accordance with some embodiments. One or more components of the system 1000 may be used for implementing any system, apparatus, detector, calculator, sources, or device mentioned above or below, or parts of such systems, apparatuses, detectors, calculators, sources, or devices, such as for example any of the above or below mentioned light source 114, light detector 116, temperature calculator 118, an FTIR system, an FTIR-ATR system, an ATR system, and the like. However, the use of the system 1000 or any portion thereof is certainly not required.

By way of example, the system 1000 may comprise a controller or processor module 1012, memory 1014, a user interface 1016, and one or more communication links, paths, buses, or the like 1018. A power source or supply 1040 is included or coupled with the system 1000. The controller 1012 can be implemented through one or more processors, microprocessors, central processing unit, logic, local digital storage, firmware and/or other control hardware and/or software, and may be used to execute or assist in executing the steps of the processes, methods and techniques described herein, and control various programs, activations, detections, calculations, calibrations, adjustments, etc. Further, in some embodiments, the controller 1012 can be part of a control system 1010 and/or implemented through one or more processors with access to one or more memory 1014. The user interface 1016 can allow a user to interact with the system 1000 and receive information through the system. In some instances, the user interface 1016 includes a display 1022 and/or one or more user inputs 1024, such as keyboard, mouse, track ball, buttons, touch screen, etc., which can be part of or wired or wirelessly coupled with the system 1000.

Typically, the system 1000 further includes one or more communication interfaces, ports, transceivers 1020 and the like allowing the system 1000 to communicate over a communication bus, a distributed network, a local network, the Internet, communication link 1018, other networks, or other communication channels with other devices and/or other such communications or combinations thereof. Further the transceiver 1020 can be configured for wired, wireless, optical, fiber optical cable, or other such communication configurations or combinations of such communications. For example, the transceiver may be configured to enable communication between the light source 114, light detector 116, temperature calculator 118, one or more ambient temperature measurement apparatuses and/or sensors, external memory, other processing devices, the Internet, and/or other such communications. Additionally or alternatively, some embodiments include one or more I/O interfaces 1034, ports or the like, allowing the system 1000 to cooperate with one or more external devices, such as one or more ambient temperature sensors, an FTIR-ATR, other sensors, external controller, and the like.

The system 1000 comprises an example of a control and/or processor-based system with the controller 1012. Again, the controller 1012 can be implemented through one or more processors, controllers, central processing units, logic, software and the like. Further, in some implementations the controller 1012 may provide multiprocessor functionality. Additionally, in some implementations, the controller 1012 is part of and/or implements an FTIR-ATR system.

The memory 1014, which can be accessed by the controller 1012, typically includes one or more processor readable and/or computer readable media accessed by at least the controller 1012, and can include volatile and/or nonvolatile media, such as RAM, ROM, EEPROM, flash memory and/or other memory technology. Further, the memory 1014 is shown as internal to the system 1010; however, the memory 1014 can be internal, external or a combination of internal and external memory. Similarly, some or all of the memory 1014 can be internal, external, or a combination of internal and external memory of the controller 1012. The external memory can be substantially any relevant memory such as, but not limited to, one or more of flash memory secure digital (SD) card, universal serial bus (USB) stick or drive, other memory cards, hard drive, and other such memory or combinations of such memory. The memory 1014 can store code, software, executables, scripts, data, parameters, conditions, sensor data, programming, programs, log or history data, user information, and the like.

One or more of the embodiments, methods, processes, approaches, and/or techniques described above or below may be implemented in one or more computer programs executable by a processor-based system. By way of example, such a processor based system may comprise the processor based system 1000, a computer, FTIR-ATR, light source, light detector, temperature calculator, etc. In another approach, the temperature calculator may be embodied in its own processor based system or incorporated with other elements into a single processor based system. Such a computer program may be used for executing various steps and/or features of the above or below described methods, processes, and/or techniques. That is, the computer program may be adapted to cause or configure a processor-based system to execute and achieve the functions described above or below. For example, such computer programs may be used for implementing any embodiment of the above or below described steps, processes, or techniques for detecting and/or determining temperature on microscales and/or nanoscales. As another example, such computer programs may be used for implementing any type of tool or similar utility that uses any one or more of the above or below described embodiments, methods, processes, approaches, and/or techniques. In some embodiments, program code modules, loops, subroutines, etc., within the computer program may be used for executing various steps and/or features of the above or below described methods, processes, and/or techniques. In some embodiments, the computer program may be stored or embodied on a computer readable storage or recording medium or media, such as any of the computer readable storage or recording medium or media described herein.

Accordingly, some embodiments provide a processor or computer program product comprising a medium configured to embody a computer program for input to a processor or computer and a computer program embodied in the medium configured to cause the processor or computer to perform or execute steps comprising any one or more of the steps involved in any one or more of the embodiments, methods, processes, approaches, and/or techniques described herein. For example, some embodiments provide one or more computer-readable storage mediums storing one or more computer programs for use with a computer simulation, the one or more computer programs configured to cause a computer and/or processor based system to execute one or more of the steps comprising: determining, from detected reflected light, light coupling to one or more phonon polariton modes from the resonant cavity; calculating a quality factor as a function of a frequency spectrum of at least one of the one or more phonon polariton modes; and determining a temperature of a dielectric material within the resonant cavity as a function of the quality factor.

Exemplary processes and/or methods are representatively described above based on one or more flow diagrams representing sequences of actions and/or communications that include one or more steps, subprocesses, communications, and/or other such representative divisions of the processes, methods, etc. These steps, subprocesses, or other such actions can be performed in different sequences without departing from the scope of the processes, methods and apparatuses. Additionally or alternatively, one or more steps, subprocesses, actions, etc. can be added, removed, or combined in some implementations.

In an application of some embodiments, cavities can be formed in $SiO_2$ wafers being processed and temperatures sensed during wafer processing. Similarly, in an application of some embodiments for high power devices, cavities can be formed in SiC or GaN wafers being processed for high power devices, and temperatures sensed during wafer processing.

This description is not to be taken in a limiting sense, but is made merely for the purpose of describing the general principles of exemplary embodiments. The scope of the invention should be determined with reference to the claims. Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

The embodiments shown in the drawings, and as described above are merely for illustrative purposes and not intended to limit the scope of the invention. Moreover, those skilled in the art will recognize that a wide variety of modifications, alterations, and combinations can be made with respect to the above described embodiments without departing from the scope of the invention as set forth in the claims, and that such modifications, alterations, and combinations are to be viewed as being within the ambit of the inventive concept.

What is claimed is:

1. A phonon based temperature measuring apparatus, comprising:
   a light source positioned to direct a light toward a prism-resonant cavity interface of an optical resonant cavity inducing an evanescent wave that is guided into the resonant cavity having surface phonon polariton properties;
   a detector positioned proximate the resonant cavity and configured to detect reflected light from the prism-resonant cavity interface; and
   a temperature calculator operatively coupled to the detector and configured to determine evanescent light coupling to one or more phonon polariton modes from the resonant cavity, calculate a quality factor as a function of a frequency spectrum of at least one of the one or more phonon polariton modes, and determine a temperature of a dielectric material within the resonant cavity as a function of the quality factor.

2. The temperature measuring apparatus of claim 1, further comprising:
one or more ambient temperature measurement apparatuses operatively coupled to the temperature calculator and configured to provide ambient temperature data to the temperature calculator, wherein the temperature calculator is configured to calibrate temperature measurements as a function of the ambient temperature data.

3. The temperature measuring apparatus of claim 2, wherein the temperature calculator is further configured to determine temperatures of dielectric material within each of one or more additional resonant cavities, and to calibrate temperature measurements as a function of the determined temperatures of the dielectric material within each of the one or more additional resonant cavities and the ambient temperature data.

4. The temperature measuring apparatus of claim 1, wherein the temperature calculator is further configured to determine temperatures of dielectric material within each of one or more additional resonant cavities, and to calibrate temperature measurements as a function of the determined temperatures of the dielectric material within each of the one or more additional resonant cavities.

5. The temperature measuring apparatus of claim 1, further comprising:
the resonant cavity comprising:
a substrate having the surface phonon polariton properties;
opposing reflective walls extending from a substrate surface of the substrate, wherein each of the reflective walls comprises a reflective surface with the reflective surfaces being separated by a width of the resonant cavity and configured to retain the dielectric material within the resonant cavity.

6. The temperature measuring apparatus of claim 5, wherein the substrate comprises silicon dioxide, and wherein the opposing walls comprise a chromium base secured to the substrate and gold extensions secured with and extending from the chromium base, wherein each of the gold extensions comprises one of the reflective surfaces.

7. The temperature measuring apparatus of claim 5, wherein the reflective surfaces are gold secured relative to the substrate surface.

8. The temperature measuring apparatus of claim 5, wherein the width of the resonant cavity is less than 2000 µm.

9. The temperature measuring apparatus of claim 1, wherein the light source is configured to direct a p-polarized infrared light toward the prism-resonant cavity interface with an evanescent field injected into the resonant cavity; and
wherein the temperature calculator, in calculating the quality factor, is configured to calculate the quality factor as a function of the frequency spectrum of a surface phonon polariton mode response from the resonant cavity induced from the p-polarized infrared light.

10. The temperature measuring apparatus of claim 9, wherein the temperature calculator, in determining the light coupling to the one or more phonon polariton modes from the resonant cavity, is configured to determine light coupling to at least a transverse optical (TO) surface phonon polariton mode and to calculate the quality factor as a function of frequency spectrum of the transverse optical surface phonon polariton mode.

11. The temperature measuring apparatus of claim 1, wherein the temperature calculator is configured to detect a light coupling to at least a transverse optical (TO) phonon polariton mode as a dip in a reflection spectra of a frequency pulse, evaluate the frequency pulse, and determine a full-width-half-maximum frequency range ($\Delta\omega$) and a dip minimum frequency ($\omega_0$) of the frequency pulse, and calculate the quality factor as a function of a ratio of the dip in minimum frequency ($\omega_0$) and the full-width-half-maximum frequency range ($\Delta\omega$).

12. The temperature measuring apparatus of claim 1, wherein the temperature calculator is configured to calculate the temperature (T) of the dielectric material as a function of the quality factor (Q) in accordance with:

$$Q = A(w_0 CT)^{-\alpha}$$

wherein A is a surface phonon-polariton resonant cavity specific constant, $w_0$ defines a known optical path length at a known temperature, C is a constant over a predefined range of temperatures from a known equilibrium temperature, and a is a surface phonon-polariton resonant cavity specific scaling constant.

13. The temperature measuring apparatus of claim 1, wherein the temperature calculator in determining the temperature of the dielectric material within the resonant cavity as a function of the quality factor is configured to determine a change in temperature from a known equilibrium temperature.

14. A method of measuring nanoscale temperature, comprising:
directing light toward a prism-resonant cavity interface having surface phonon polariton properties;
detecting, in response to the light being directed toward the prism-resonant cavity interface, reflected light;
determining, from the detected reflected light, light coupling to one or more phonon polariton modes from the resonant cavity;
calculating a quality factor as a function of a frequency spectrum of at least one of the one or more phonon polariton modes; and
determining a temperature of a dielectric material within the resonant cavity as a function of the quality factor.

15. The method of claim 14, further comprising:
obtaining temperature data corresponding to one or more ambient temperatures external to the resonant cavity;
calibrating the determined temperature of the dielectric material as a function of the temperature data corresponding to the one or more ambient temperatures.

16. The method of claim 15, further comprising:
determining a quality factor corresponding to each of one or more additional resonant cavities formed on a substrate on which the resonant cavity is formed, wherein at least one of the one or more additional resonant cavities has a width different than a width of the resonant cavity;
wherein the temperature calculator is further configured to determine temperatures of a dielectric material within each of the one or more additional resonant cavities; and to calibrate the temperature measurements as a function of the determined temperature of the dielectric material within each of the one or more additional resonant cavities and the ambient temperature data.

17. The method of claim 14, wherein the determining the light coupling to the one or more phonon polariton modes from the resonant cavity comprises determining light coupling to a transverse optical (TO) surface phonon polariton mode, and wherein the calculating the quality factor comprises calculating the quality factor as a function of a frequency spectrum of the transverse optical surface phonon polariton mode.

18. The method of claim 14, wherein the determining the light coupling to the one or more phonon polariton modes comprises detecting the light coupling to transverse optical (TO) phonon modes as a dip in a reflection spectra of a frequency pulse; and wherein the calculating the quality factor comprises:
determining a full-width-half-maximum frequency range ($\Delta\omega$) of the frequency pulse;
determining a dip minimum frequency ($\omega_0$) of the frequency pulse; and
calculating the quality factor as a function of a ratio of the dip minimum frequency ($\omega_0$) and the full-width-half-maximum frequency range ($\Delta\omega$).

19. The method of claim 14, wherein the determining the temperature (T) comprises calculating the temperature of the dielectric material as a function of the quality factor (Q) in accordance with:

$$Q = A(w_0 CT)^{-\alpha}$$

wherein A is a surface phonon-polariton resonant cavity specific constant, $w_0$ defines a known optical path length at a known temperature, C is a constant over a predefined range of temperatures from a known equilibrium temperature, and a is a surface phonon-polariton resonant cavity specific scaling constant.

20. The method of claim 14, further comprising:
generating a p-polarized infrared light, wherein the directing the light into the cavity comprises directing the p-polarized infrared light into the cavity; and
wherein the calculating the quality factor comprises calculating the quality factor as a function of the frequency spectrum of the surface phonon polariton mode response from the resonant cavity induced from the p-polarized infrared light.

21. The method of claim 14, wherein the determining the temperature of the dielectric material comprises determining a change in temperature from a known equilibrium temperature, wherein the change in temperature is less than about 1° C.

22. The method of claim 14, wherein the determining the temperature of the dielectric material comprises determining a change in temperature from a known equilibrium temperature.

* * * * *